(12) United States Patent
Ruud

(10) Patent No.: US 6,493,420 B2
(45) Date of Patent: Dec. 10, 2002

(54) APPARATUS AND METHOD FOR IN-SITU MEASUREMENT OF RESIDUAL SURFACE STRESSES

(75) Inventor: Clayton O. Ruud, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/908,659

(22) Filed: Jul. 18, 2001

(65) Prior Publication Data

US 2002/0051514 A1 May 2, 2002

Related U.S. Application Data

(60) Provisional application No. 60/219,997, filed on Jul. 21, 2000.

(51) Int. Cl.[7] .............................................. G01N 23/20
(52) U.S. Cl. ............................ 378/72; 378/70; 378/71; 378/86
(58) Field of Search ............................ 378/70, 71, 72, 378/86

(56) References Cited

U.S. PATENT DOCUMENTS

| | | | |
|---|---|---|---|
| 4,489,425 A | 12/1984 | Borgonovi | 378/72 |
| 4,686,631 A | 8/1987 | Ruud | 364/508 |
| 5,148,458 A | * 9/1992 | Ruud | 378/70 |
| 5,414,747 A | * 5/1995 | Ruud et al. | 378/72 |
| 5,724,401 A | 3/1998 | Kurtz et al. | 378/17 |
| 5,784,432 A | 7/1998 | Kurtz et al. | 378/72 |
| 5,828,724 A | 10/1998 | Kurtz | 378/70 |
| 6,058,160 A | 5/2000 | Kurtz | 378/70 |

OTHER PUBLICATIONS

Ruud, "X–Ray Analysis and Advances in Portable Field Instrumentation," *Journals of Metals*, pp. 10–15 (Jun. 1979).
Ruud, et al., "A Miniature Instrument for Residual Stress Measurement," *Advances in X–Ray Analysis*, vol. 27 (1984).
Ruud, "A Review of Nondestructive Methods for Residual Stress Measurement," *J. of Metals*, vol. 33 (7): pp. 35–40 (Jul. 1981).
SAE, *Residual Stress Measurement by X–Ray Diffraction*, SAE J784a, Soc. Auto Eng. Handbook Supplement (Aug. 1971).

* cited by examiner

*Primary Examiner*—Robert H. Kim
*Assistant Examiner*—Courtney Thomas
(74) *Attorney, Agent, or Firm*—Pennie & Edmonds LLP

(57) ABSTRACT

An apparatus for in-situ measurement of residual surface stresses comprises a compact x-ray tube and a detector. X-rays emitted by the x-ray tube are diffracted from a specimen surface and intercepted by the detector. The intercepted x-rays are converted into light and transferred by a first fiber optic bundle and a second fiber optic bundle to light detection devices. Intensities of the received light are digitized by the light detection devices to generate a first ring and a second ring with common centers. The residual stress in the specimen surface is calculated based on a difference between the radii of the first ring and the second ring.

26 Claims, 10 Drawing Sheets

APPARATUS AND METHOD FOR IN-SITU MEASUREMENT OF RESIDUAL SURFACE STRESSES

CROSS REFERENCE TO RELATED APPLICATION

This application claims priority from the Provisional Application entitled "Apparatus and Method for In-Situ Measurement of Residual Surface Stresses", U.S. Serial No. 60/219,997, filed on Jul. 21, 2000.

BRIEF DESCRIPTION

This invention relates generally to measurement of surface stresses. More particularly, this invention relates to in-situ measurement of residual surface stresses.

BACKGROUND

Residual surface stresses have been shown to play a critical role in the stress corrosion cracking of many metal or polycrystalline components in a wide array of devices, such as power plant components (e.g., condenser tubes, steam generator U-bends, expansion transitions, girth welds, etc.). One generally reliable technique to measure residual stress in polycrystalline materials is based on diffraction. The diffraction technique exploits the fact that when a metallic crystalline material is stressed, the elastic strains in the material are manifested in the crystal lattice of its grains. The stress, applied externally or residual within the material, if below its yield strength, is taken up by interatomic elastic macro strain that is spread over several tens of grains. As a result of stress, the distance between lattice planes (i.e., the d-spacing) and the angle ($2\theta$) at which radiation is diffracted are changed. That is, diffracted radiation peak position shifts and therefore the elastic strain experienced by the specimen can be quantified.

Generally, there are two types of radiation that have been applied to stress measurement by diffraction, namely, x-ray and neutron radiation. Unfortunately, neutron radiation does not provide for in-situ or surface measurement. Further, existing x-ray diffraction instruments are generally too bulky for good portability to be applied in-situ.

Pennsylvania State University has developed a fiber optic based x-ray detector technology, called the Ruud-Barrett Position Sensitive Scintillation Detector (PSSD). The PSSD uses two independent detection surfaces to collect data from two positions on a diffracted x-ray ring simultaneously, thus, providing a unique capability of precision stress measurement by the single exposure technique. The single exposure technique is based on the fact that a single incident x-ray beam is diffracted at a given $\theta$ angle or small range of $\theta$ angles, such that a cone of diffracted beams is formed. A plane perpendicular to the cone axis intercepts the cone as a circle when the specimen surface is unstressed, and as a distorted ellipse, when the specimen surface is stressed. The distortion of the ellipse is a measure of that surface stress.

The PSSD uses flexible coherent fiber optic bundles about one meter in length and 3 millimeters by 12 millimeters in cross section to conduct an optical analog of the diffracted x-ray pattern to an electronic component of the PSSD where the pattern is amplified and digitized. Optical signal is produced by the diffracted x-ray pattern striking a scintillation coating where the x-rays are converted to light. This light analogue of the x-ray pattern is transported via the flexible, coherent fiber optic bundles to the electronic component of the PSSD that is usually one or more meters away from the specimen. In the electronic component of the PSSD, the optical signal is amplified by an image intensifier, then converted into a digital electronic signal by diode arrays. The digital electronic signal is then used by a computer to calculate the stress on the specimen surface.

Presently the PSSD instruments are limited to insertion in pipes no smaller than 10 centimeters in diameter and requires that a 200-watt x-ray tube be brought in close proximity (e.g., 4 centimeters) of the surface to be measured. The present PSSD faces several barriers to further miniaturization and improved portability. First, the cross section of the bundle is too large to be used for inside specimen with diameters less than about 7 centimeters even if the size of the x-ray source is significantly reduced. Second, if the fiber optics were reduced in cross-section, the spatial resolution of the diode arrays presently used may be too coarse to provide adequate precision of x-ray stress measurement. Additional information about the PSSD is disclosed in U.S. Pat. Nos. 4,686,631 and 5,148,458. These patents are hereby incorporated by reference for all purposes.

Based on the foregoing, a need arises for an improved PSSD that is easily portable and is capable of measuring stresses between two parallel plates that are a small distance (e.g., about 5 centimeters) apart.

SUMMARY

An apparatus for in-situ measurement of residual surface stresses comprises a compact x-ray tube and a detector. In an exemplary embodiment, the detector includes a tube sleeve coupled to the compact x-ray tube, a first fiber optic bundle coupled to the tube sleeve, a second fiber optic bundle coupled to the tube sleeve, and a charged coupled device coupled to the fiber optic bundles. An alternative embodiment consisting of incorporating the fiber optic holders and colimator into the x-ray tube body is also envisioned. X-rays emitted by the x-ray tube are diffracted from a specimen surface and intercepted by the first fiber optic bundle and the second fiber optic bundle. The intercepted x-rays are converted into light and transferred by the first fiber optic bundle and second fiber optic bundle to the charged coupled device. Intensities of the received light are detected and digitized to generate a first ring and a second ring. The residual stress in the specimen surface is calculated based on a difference between the radii of the first ring and the second ring.

In an exemplary embodiment, the detector further comprises scintillators attached to the front end of the first fiber optic bundle and the second fiber optic bundle for converting the x-rays into light. In one embodiment, the scintillators are rare earth scintillators. In another embodiment, the scintillators are cadium zinc scintillators.

In another exemplary embodiment, the detector further comprises an image intensifier positioned between both the first fiber optic bundle and the charged coupled device and the second fiber optic bundle and the charged coupled device. The image intensifiers amplify light received from the first fiber optic bundle and the second fiber optic bundle, respectively.

In yet another exemplary embodiment, the detector further comprises a collimator attached to the tube sleeve for collimating x-rays emitted from the x-ray tube onto the specimen surface.

In an exemplary embodiment, the compact x-ray tube is less than 1 inch in diameter, generates 20 kilovolt x-rays, and requires less than 100 watts. In another exemplary embodiment, the first fibers bundle and the second fiber optic bundle comprise fibers each of approximately 10 microns in size and each bundle has a cross section of approximately 6 mm by 6 mm.

In one embodiment, the first fiber optic bundle is split into two bundles to fit along the compact x-ray tube and is rejoined behind the cathode end of the compact x-ray tube. In another embodiment, the first fiber optic bundle is contoured to fit closely near the compact x-ray tube.

In an exemplary embodiment, the charged coupled device comprises a plurality of pixels and each pixel is capable of detecting photons striking the surface of that pixel. In one embodiment, residual stress on the specimen surface is calculated by a computer attached to receive digitized data from the charged coupled device.

A method for in-situ measurement of residual surface stresses comprises the steps of intercepting a first segment of x-rays diffracted from a specimen surface, intercepting a second segment of x-rays diffracted from the specimen surface, converting the segments into light, detecting intensities in the light from the first segment via a charged coupled device, detecting intensities in the light from the second segment via a charged coupled device, defining a first and second ring based on the intensities detected and a common center calculating a first radius of the first ring, calculating a second radius of the second ring, calculating a difference between the first radius and the second radius, and calculating residual stress in the specimen surface based on the difference.

In an exemplary embodiment, the step of converting the segments into light includes the steps of converting the first segment into light via a first scintillation coating and converting the second segment into light via a second scintillation coating. In another exemplary embodiment, the method further comprises the steps of amplifying the light converted by the first scintillation coating via an image intensifier and amplifying the light converted by the second scintillation coating via an image intensifier.

In another exemplary embodiment, the step of defining a first ring includes the steps of fitting the intensities detected by the charged coupled device into a set of curves, determining apexes in the set of curves, and connecting the apexes to define the first ring.

In yet another exemplary embodiment, the step of defining a second ring includes the steps of fitting the intensities detected by the charged coupled device into a set of curves, determining apexes in the set of curves, and connecting the apexes to define the second ring.

DETAILED DESCRIPTION

The Improved PSSD

Figure 1:
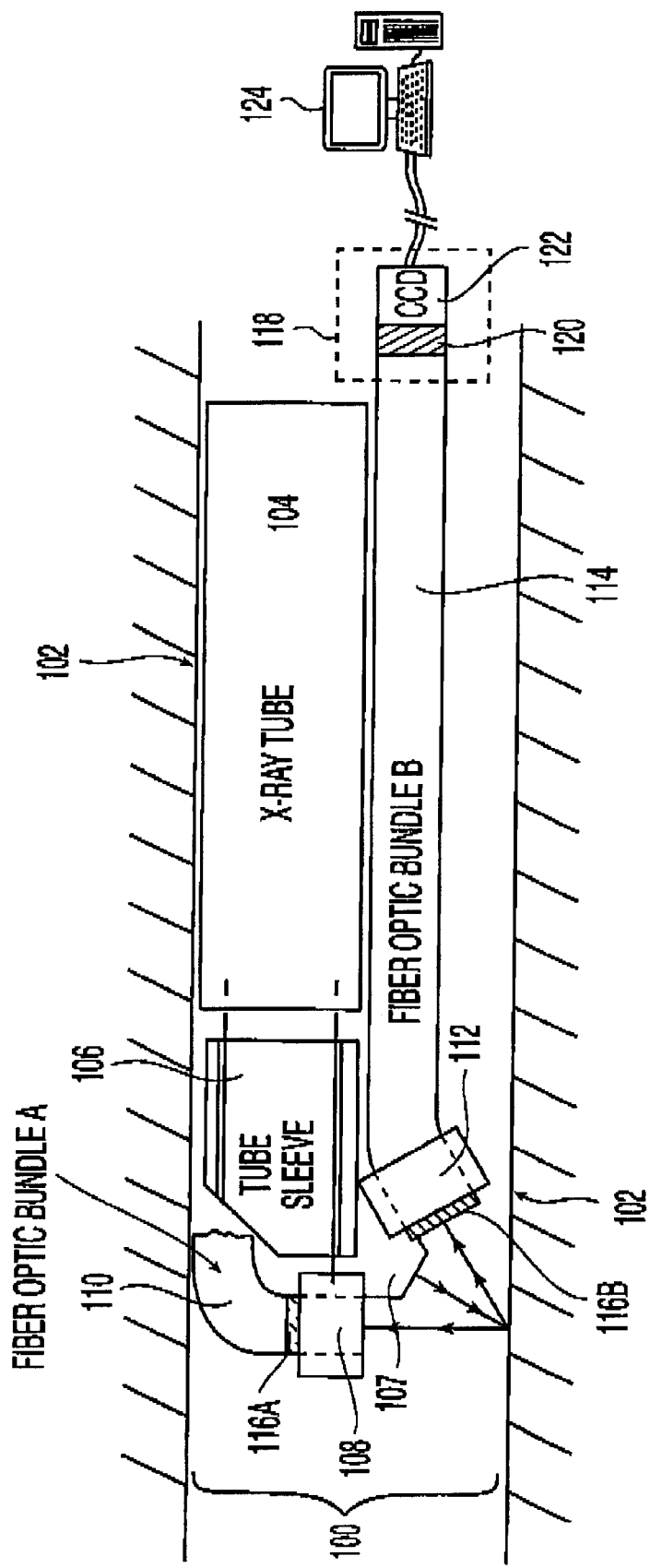
FIG. 1 illustrates an exemplary in-situ residual stress measuring device in accordance with an embodiment of the invention.

FIG. 1 illustrates an exemplary in-situ residual stress measuring device 100 (hereinafter "the improved PSSD") in accordance with an embodiment of the invention. The improved PSSD 100 is inserted into a specimen tube 102 having a specimen surface whose stress is to be measured.

The improved PSSD 100 includes a compact x-ray tube 104, a tube sleeve 106 coupled to the anode end of the x-ray tube 104, a collimator 107, a fiber optic bundle holder A 108 (hereinafter "holder A") holding a fiber optic bundle A 110, a fiber optic bundle holder B 112 (hereinafter "holder B") holding a fiber optic bundle B 114, scintillation coating layers 116A and 116B for the fiber optic bundle A 110 and fiber optic bundle B 114, respectively, and an electronic component 118. For ease of explanation, FIG. 1 only shows the electronic component 118 attached to the fiber optic bundle B 114.

In an exemplary embodiment, the electronic component 118 includes an image intensifier 120 coupled to a charged coupled device (CCD) 122 for detecting light received via the fiber optic bundle B 114. Although not shown, the fiber optic bundle A 110 is attached to the image intensifier 120 and charged coupled device 122. The CCD 122 digitizes amplified light received from the image intensifier 120 and feeds the digitized data into a fast calculator, such as a computer 124, for calculating the residual stress on the specimen surface.

In an exemplary embodiment, the specimen tube 102 is approximately 50 mm in diameter. In this embodiment, the x-ray tube 104 is approximately 25 mm at the cathode end, approximately 18 mm at the anode end, and approximately 140 mm in total length. Other dimensions for the x-ray tube 104 is possible without departing from the essence of this invention provided that the x-ray tube is less than 1 inch in diameter, generates x-rays under a voltage of at least 20 kilovolts, and requires a wattage of less than 100 watts. A suitable x-ray tube 104 may be acquired commercially from x-ray tube manufacturers such as Proto Manufacturing Limited. Further, in this embodiment, the holder A 108 and holder B 112 have the dimensions of approximately 10 mm by 18 mm by 19 mm. In an exemplary embodiment when x-rays are emitted from the x-ray tube 104 at 60° angle relative to the vertical axis of the x-ray tube 104, the face of the holder B 112 is positioned at a 30° angle relative to the vertical axis of the x-ray tube 104. This angle is flexible depending on the angle at which the x-rays are being emitted from the x-ray tube 104 and the diffraction angle to be detected. For example, if the x-rays are emitted at 90° angle relative to the vertical axis of the x-ray tube 104, then the face of the holder B 112 should be at a 60° relative to the vertical axis of the x-ray tube 104.

The x-ray tube 104 emits x-rays via the collimator 107 onto the surface of the specimen tube 102. In an exemplary embodiment, the collimator 107 has a rectangular window having a cross-section of 1 mm by 4 mm for collimating x-rays from the x-ray tube 104. The window size of the collimator 107 is adjustable depending on striking a balance between desired sharpness and flux of the x-rays. In addition, the window does not need to be rectangular in shape and may be, for example, circular.

Collimated x-rays typically strike the specimen surface at an angle (e.g., 60°) relative to the vertical axis of the x-ray tube 104. The angle is adjustable within an acceptable range, such as 60° to 90° relative to the vertical axis of the x-ray tube 104. Upon striking the specimen surface, the x-rays are diffracted from the specimen surface and intercepted by the fiber optic bundle A 110 and the fiber optic bundle B 114. Generally, the x-rays are diffracted as x-ray cones. These x-ray cones are intercepted by the fiber optic bundles 110, 114 at certain locations along the cones. For example, if an x-ray cone is intercepted in a plane that is perpendicular to the cone's axis, a ring of x-rays is intercepted. Note that the ring of x-rays is an ellipse when stress is present on the specimen surface. As the distance between the specimen surface and the fiber optic bundles 110, 114 decreases, a larger segment of the ring of x-rays is intercepted. Thus, such a segment can no longer be treated as a straight line as was done in the past when smaller segments were intercepted because the distance between the specimen surface and the fiber optic bundles 110, 114 was greater.

The diffracted x-rays are converted into light by the scintillation coatings 116A and 116B, respectively, located at the front end of the fiber optic bundles 110, 114. In an exemplary embodiment, the scintillation coatings 116A, 116B are made of cadium zinc scintillators. In another exemplary embodiment, the scintillation coatings 116A, 116B are made of rare earth scintillators. However, the scintillation coating may be made of any other suitable material. The thickness of the scintillation coatings is adjustable depending on a desired efficiency and resolution.

After the x-rays are converted to light by the scintillation coatings 116A and 116B, light travels through the fiber optic bundles 110, 114, respectively. In an exemplary embodiment, each fiber optic bundle is made of tens of thousands of coherent fibers. The optimum size of each fiber optic bundle is determined based on two competing considerations: (1) each fiber optic bundle should be as large as possible to capture as much of the diffracted x-rays as possible; and (2) each fiber optic bundle should be as small as possible to be able to fit inside a very confined area (e.g., a 50 mm tube). For example, to achieve a good trade-off among the considerations above when fitting fiber optic bundles 110, 114 into a 50 mm tube, each fiber optic bundle 110, 114 may have a cross section of 6 mm×6 mm.

Light traveled through the fiber optic bundles 110, 114 are received at the end of the bundles by an image intensifier 120. The image intensifier 120 amplifies the received light then feed the amplified light into a charged coupled device 122. The charged coupled device 122 comprises pixels, where each pixel acting as a tiny detector that detects the number of photons striking its surface. Generally, a suitable charged coupled device 122 for purposes of the improved PSSD 100 is commercially available.

Photons detected by the charged coupled device 122 for each fiber optic bundle 110, 114 are digitized and later used to generate a segment of the ring of x-rays. Because the improved PSSD 100 is capable of fitting into a much more confined space than stress measuring devices previously available and the distance from the scintilation coatings 116A and 116B to the irradiated specimen surface 102 is much smaller, larger segments of the diffracted x-ray cone are expected to be intercepted and ultimately detected by the charged coupled devices 122. As a result, the larger segments of the diffracted x-rays should be treated as two dimensional rings. In order to calculate stress based on intercepted two dimensional rings, charged coupled devices 122 are preferred over the prior implementation of diode arrays. This is because diode arrays are linear arrays having only one dimension while charged coupled devices 122 are area arrays having two dimensions, which is preferred for detecting rings. Various properties of the detected rings are subsequently used by a fast calculator, such as the computer 124, to calculate the residual stress on the specimen surface as described below.

Stress Analysis

After a ring from each fiber optic bundle 110, 114 has been detected and digitized, the radii of the two rings are determined. The radii of the rings are used to calculate the residual surface stress of the specimen surface as described below.

Figure 1A:
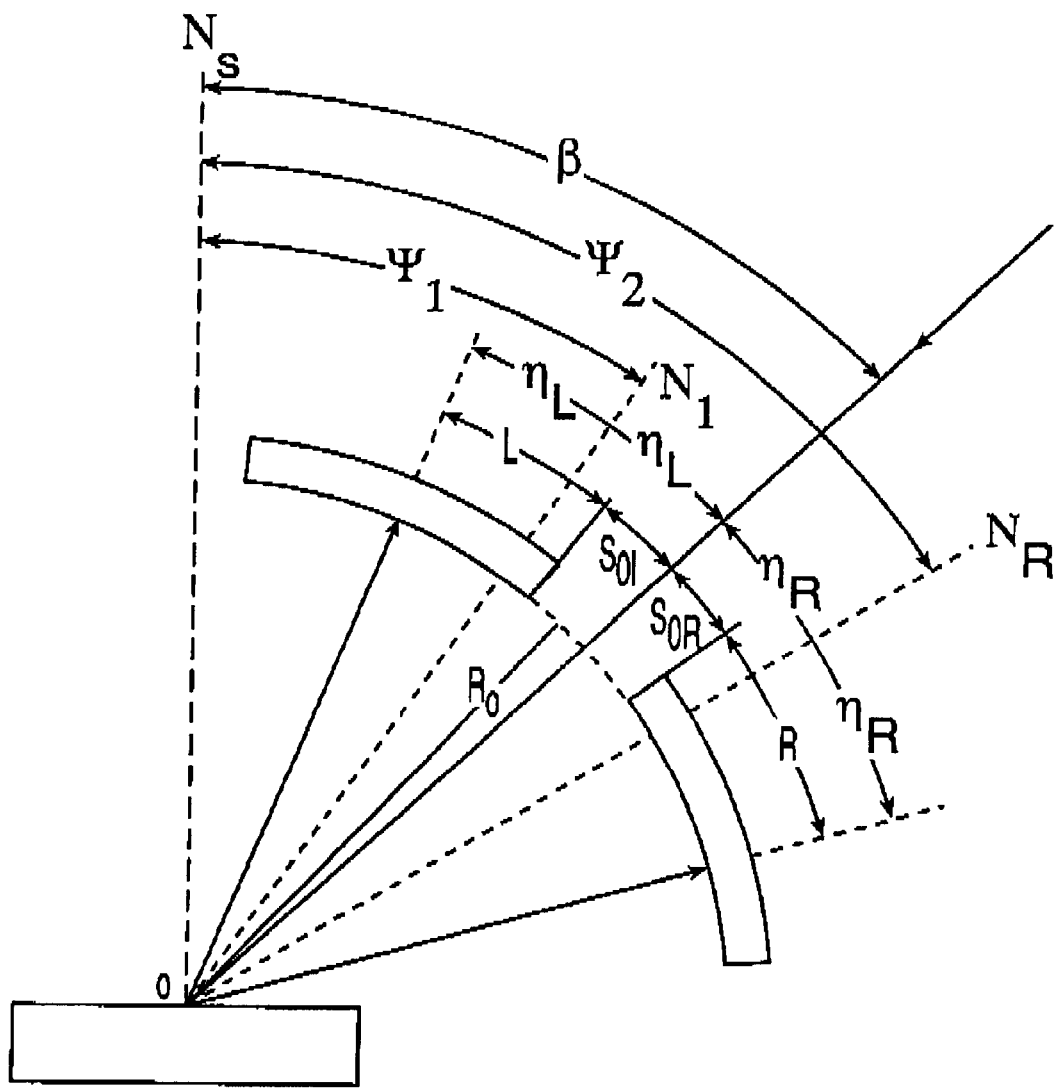
FIG. 1a illustrates various angles of diffraction of x-rays from a surface.

For a single exposure, the stress in a specimen surface can be calculated by the following equation (eq. 1):

$$\sigma \cong \frac{E}{(1+v)} \frac{\Delta 2\theta}{4\sin 2\beta \sin^2\theta} = \frac{-E}{(1+v)} \frac{\Delta 2\eta}{4\sin 2\beta \sin^2\theta} \quad (\text{eq. 1})$$

where E is the Young's modulus, v is Poisson's ratio, and the angles $\beta$, $2\theta$, and $2\eta$ are defined in FIG. 1a, which represents the diffraction of x-rays from a specimen surface.

Next, a small angle approximation process known in the art is applied, such that: $\Delta 2\eta = \tan^{-1}\{(L'+S_{ol}')\kappa/R_o\}_{-tan}^{-1}\{(R'+S_{ol}')\kappa/R_o\} \approx [(L'S_{ol}') - (R'+S_{or}')]\kappa/R_o$, where L', $S_{ol}'$, R' and $S_{or}'$ are in pixels, and $\kappa$ is the number of degrees per pixel, assuming that the detector face is curved (i.e., the faces of the fiber optic bundle A 110 and B 114 are flat). The equation (1) is then reduced to:

$$\sigma \approx \frac{E}{1+v}\left\{\frac{[(L'+S_{ol}') - (R'+S_{or}')] \times \kappa}{4R_o \sin 2\beta \sin^2\theta}\right\} \quad (\text{eq. 2})$$

where $R_o$ is the working distance, also called specimen-to-detector distance (i.e., the distance between the specimen surface to the faces of the scintilation coated fiber optic bundles A 110 and B 114). By measuring the shift in L', $S_{ol}'$, R' and $S_{or}'$ for known changes in $R_0$, a calibration criterion is established where the unstressed pixel location R' is determined as a function of the left pixel location L' by using a parabolic regression process known in the art (i.e., R'=AL'$^2$+BL'+C, where A, B, and C are the parabolic coefficients). This technique uses a "Predictor/Corrector" iterative solution for $R_0$ with the corrector term as a function of stress. As a result, the initial guess for $R_0$ is:

$$R_{o(1)} \frac{L + R + S_{ol} + S_{or}}{2\tan 2\eta_0} \quad \text{(eq. 3)}$$

and the iterative correction is:

$$R_{0(i+1)} = \frac{L + R + S_{ol} + S_{or}}{2\tan 2\eta_0} - \frac{L_{ERR} + R_{ERR}}{2\tan 2\eta_0} \quad \text{(eq. 4)}$$

where L and R equal radii of rings detected by charged coupled devices 122 attached to fiber optic bundles A 110 and B 114, respectively, and:

$$L_{ERR} = \frac{2\sigma(i)R_{o(i)}}{\frac{E}{1+v}\cot\theta_0}\sin^2(\Psi_L) \text{ and } R_{ERR} = \frac{2\sigma(i)Ro(i)}{\frac{E}{(1+v)}\cot\theta_o}\sin^2(\Psi_R) \quad \text{(eq. 5)}$$

Once a $R_0$ solution has converged, (considered as a change of less than 0.1% $R_0$ between iterations), surface stress is calculated by applying equation (eq. 2). While this approach has been proven to work well for large working distances (e.g., $R_0$=20 mm), when the small angle approximation process (essentially assuming that the detector is curved) is not valid (e.g., when $R_0$<20 mm), a refined methodology can be applied.

The refined methodology is accomplished by using the parabolic regression technique to determine $R_0$ as a function of $L'+R'+S_{ol}'+S_{or}'$, and the powder specimen surface values of $2\eta_{Left}$ and $2\eta_{Right}$ as functions of $R_0$. As stated before, $S_{ol}'$ and $S_{or}'$ are linear distances and are independent of changes in $R_0$. A number of diffraction measurements are taken so that the positions $S_{ol}'$ and $S_{or}'$ could be determined with minimal error. Using the values of $S_{ol}'$ and $S_{or}'$, the value $S'+R'+S_{ol}'+S_{or}'$ is determined, where $R_0$ is changed by placing a foil of known thickness under the powder specimen surface. Based on these data, the functions $R_0(S'+R'+S_{ol}'+S_{or}')$ and $2\eta_{Left}(R_0)$ and $2\eta_{Right}(R_0)$ are determined by parabolic regression.

After data collection and fitting based on digitized data from the charged coupled devices 122, $R_0$ is calculated from the value of $(S'+R'+S_{ol}'+S_{or}')$. Once $R_0$ is known, the values $2\eta_{Left}(R_0)$ and $2\eta_{Right}(R_0)$ are calculated for the powder specimen surface. Then, for the stressed material:

$$\Delta 2\eta = \{[2\eta_{Left} - 2\eta_{LeftPowder}] - [2\eta_{Right} - 2\eta_{RightPowder}]\} \quad \text{(eq.6)}$$

This value is then used in equation (eq. 1) to calculate the surface stress. By calculating values of η, taking into consideration that the detector had a non-curved face, a consistent single-exposure stress measurement is possible, even at small working distances (e.g., less than 20 mm).

Exemplary Embodiments

Figure 2:
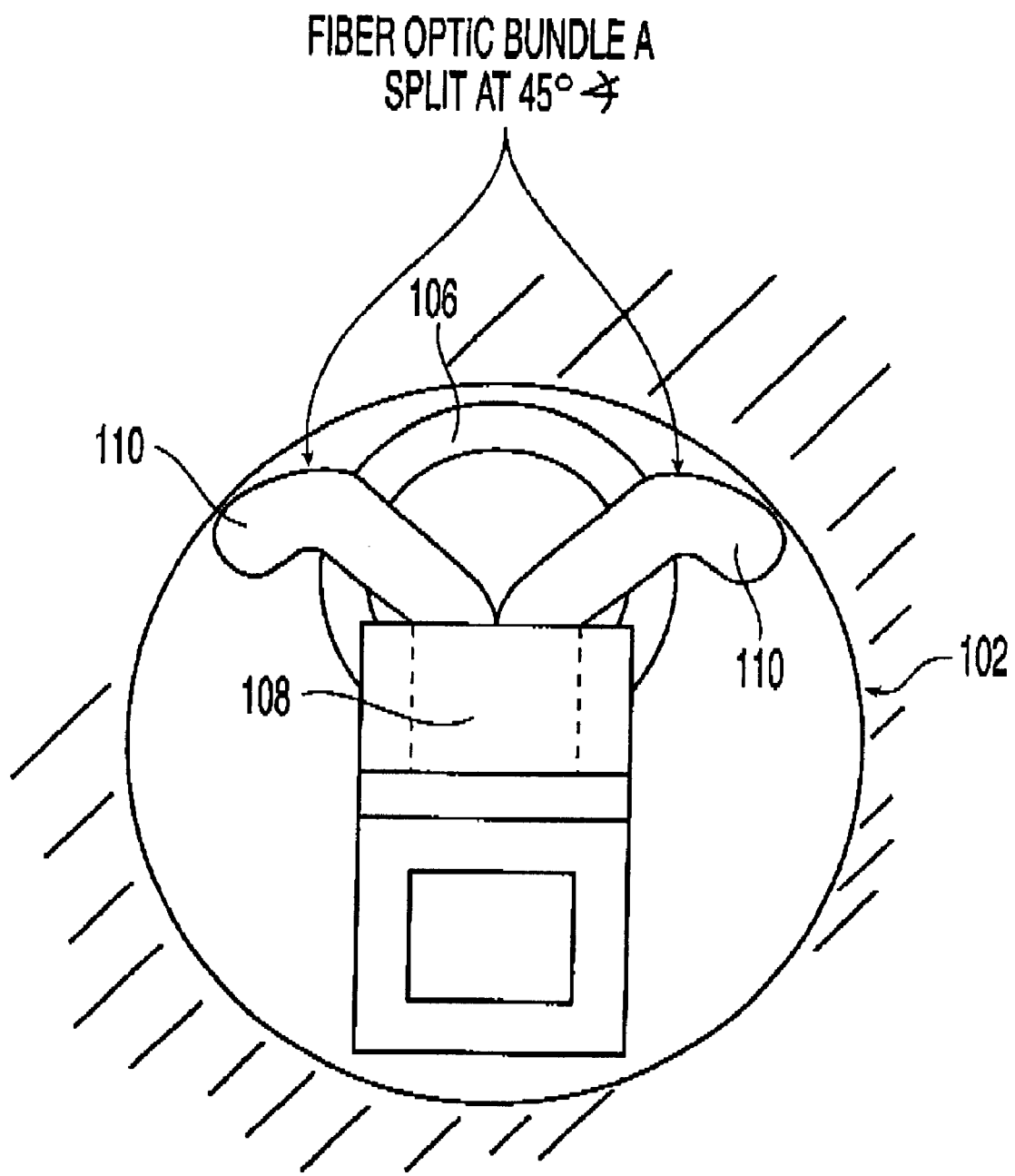
FIG. 2 illustrates a partial frontal view of an exemplary split fiber optic bundle in accordance with an embodiment of the invention.

FIG. 2 illustrates a partial front view of the improved PSSD 100 showing a split fiber optic bundle A 110 as an embodiment of the invention. In this embodiment, the fiber optic bundle A 110 is split at a 45° angle relative to the vertical axis of the x-ray tube 104. The purpose of splitting the fiber optic bundle A 110 is to ease its fit along the x-ray tube 104, reduce interference from the x-ray tube 104, and reduce the size of the improved PSSD 100. The split fiber optic bundle A 110 is later rejoined (not shown) before light is fed into the electronic component 118. In an exemplary embodiment, the angle (i.e., 45°) of the spilt of the fiber optic bundle A 110 is adjustable depending at least on the extent that the fiber optics can be bent without fracturing. Generally, it is desirable to bend the fiber optic bundle A 110 to the highest tolerable angle because this way will result in the least interference from the x-ray tube 104. In a preferred embodiment, the fiber optic bundle A 110 is wrapped underneath the x-ray tube 104, making the improved PSSD 100 most compact while incurring the least interference.

Figure 3:
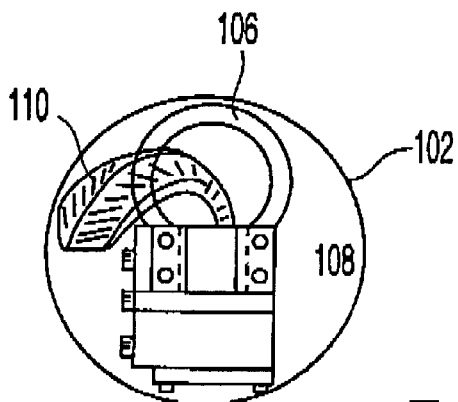
FIG. 3 illustrates a partial frontal view of another exemplary fiber optic bundle in accordance with an embodiment of the invention.

FIG. 3 illustrates another partial front view of the improved PSSD 100 to show a fiber optic bundle A 110 that is contoured as another embodiment of the invention. Instead of splitting the fiber optic bundle A 110, in this embodiment, the bundle 110 is contoured at an angle that eases its travel along the x-ray tube 104, reduces interference from the x-ray tube 104, and reduces the size of the improved PSSD 100.

Figure 4:
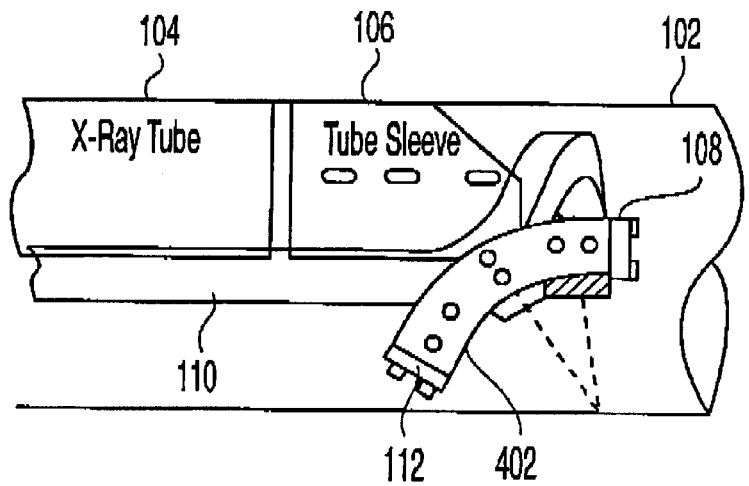
FIG. 4 illustrates a partial left view of an exemplary in-situ residual stress measuring device in accordance with an embodiment of the invention.

FIG. 4 illustrates a partial left view of the improved PSSD 100 to show the contoured embodiment as illustrated in FIG. 3 from another angle. The contour is adjustable to get the fiber optic bundle A 110 to bend as close to the x-ray tube as possible so that the improved PSSD 100 can fit into a confined space without causing any fracture in the fiber optics. This view also shows an exemplary support means 402 that is used to support holder A 108. In an exemplary embodiment, the same support may be used to support holder B 112.

Figure 5:
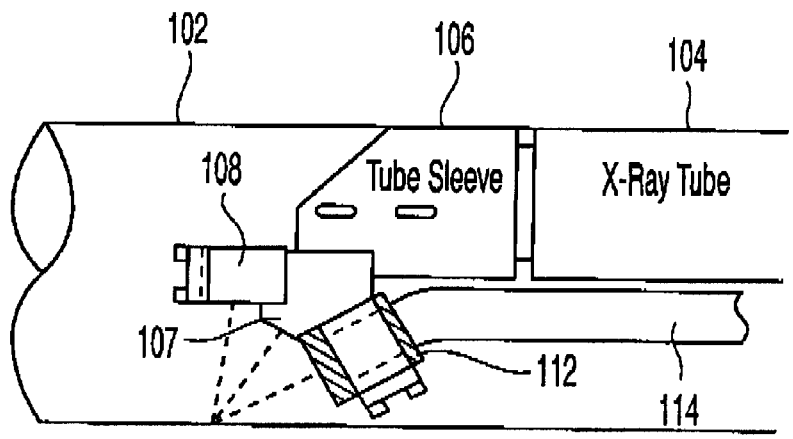
FIG. 5 illustrates a partial right view of an exemplary in-situ residual stress measuring device in accordance with an embodiment of the invention.

FIG. 5 illustrates a partial right view of the improved PSSD 100 to show the fiber optic bundle B 114 in relation to the fiber optic bundle A 110 whether the bundle A 110 is split or contoured.

Figure 6:
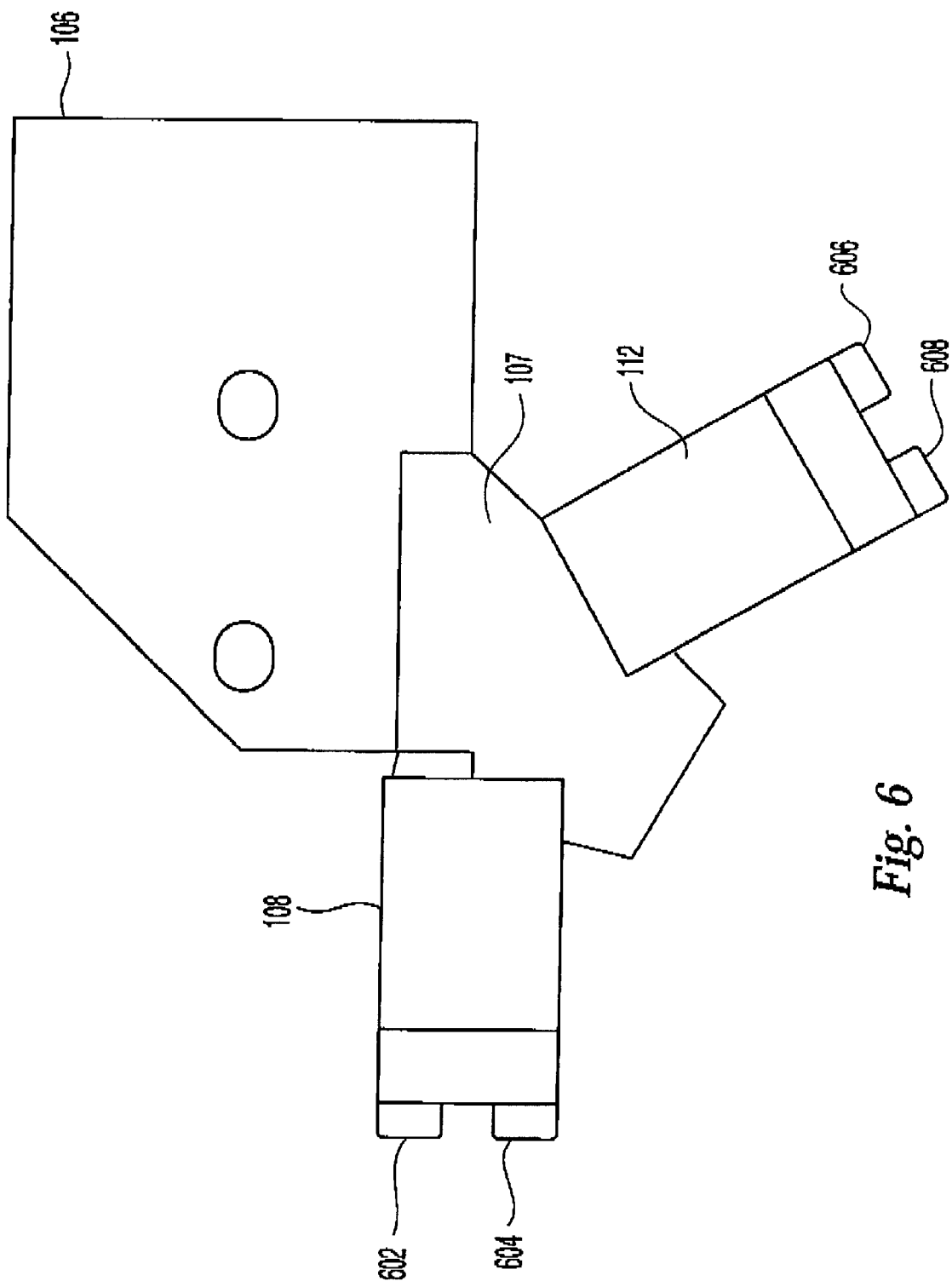
FIG. 6 illustrates a partial right view of an exemplary in-situ residual stress measuring device in accordance with an embodiment of the invention.

FIG. 6 illustrates another partial right view of the improved PSSD 100 in accordance with an embodiment of the invention. In FIG. 6, the holders 108, 112 are attached to the collimator 107 via mechanical means, such as screws 602–608.

Figure 7:
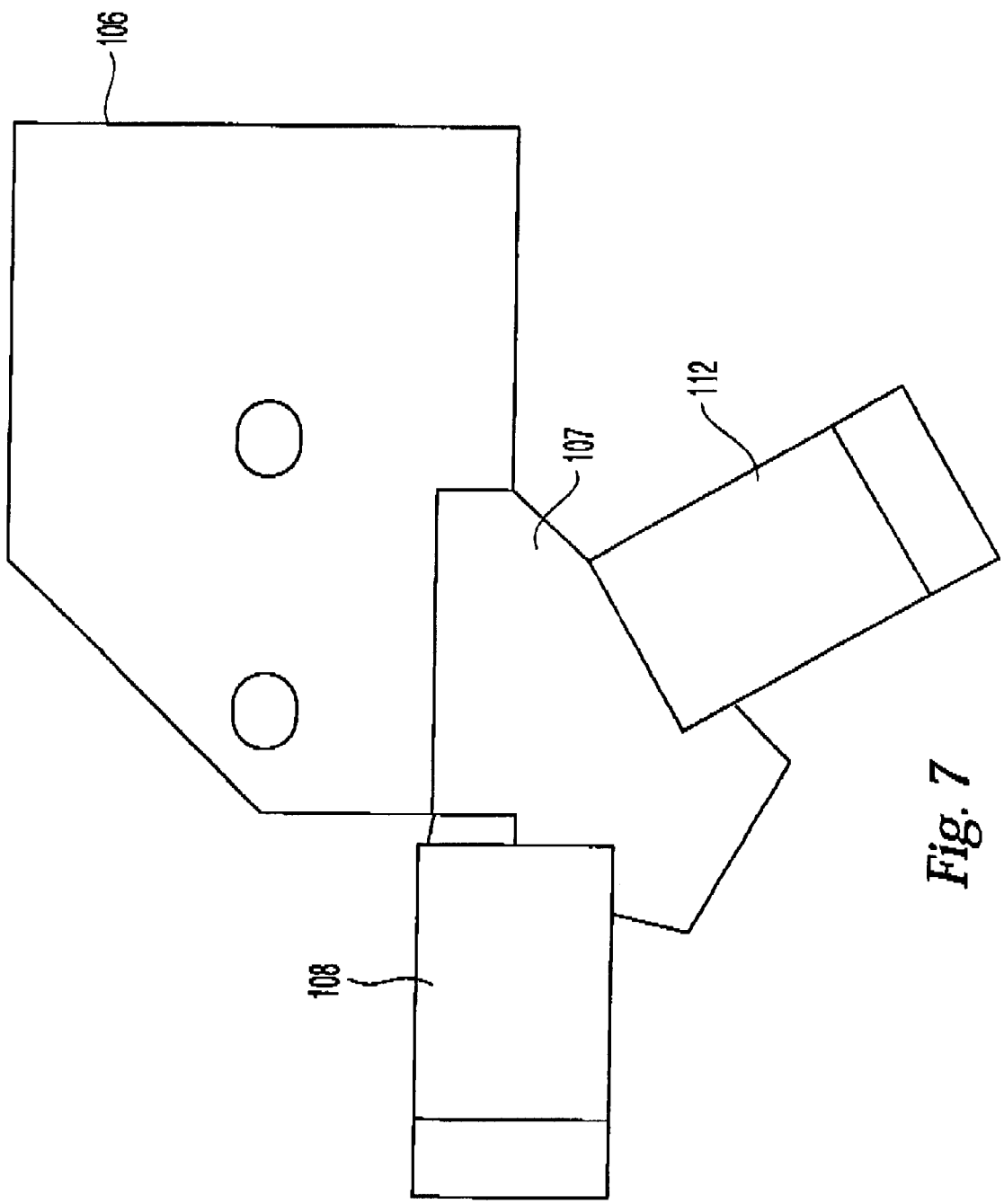
FIG. 7 illustrates another partial right view of an exemplary in-situ residual stress measuring device in accordance with an embodiment of the invention.

FIG. 7 illustrates another partial right view of the improved PSSD 100 in accordance with another embodiment of the invention. In FIG. 7, the holders 108, 112 are attached to the collimator 107 via adhesive means, such as epoxy. In an exemplary embodiment, mechanical means, such as screws 602–608, are initially used to adjust the holders 108, 112 to a desirable position. Subsequently, the screws 602–608 are replaced by adhesive means, such as epoxy. In another exemplary embodiment, the entire improved PSSD 100 is manufactured as one solid piece, thus, minimizing the need for either the mechanical means or the adhesive means.

Figure 8:
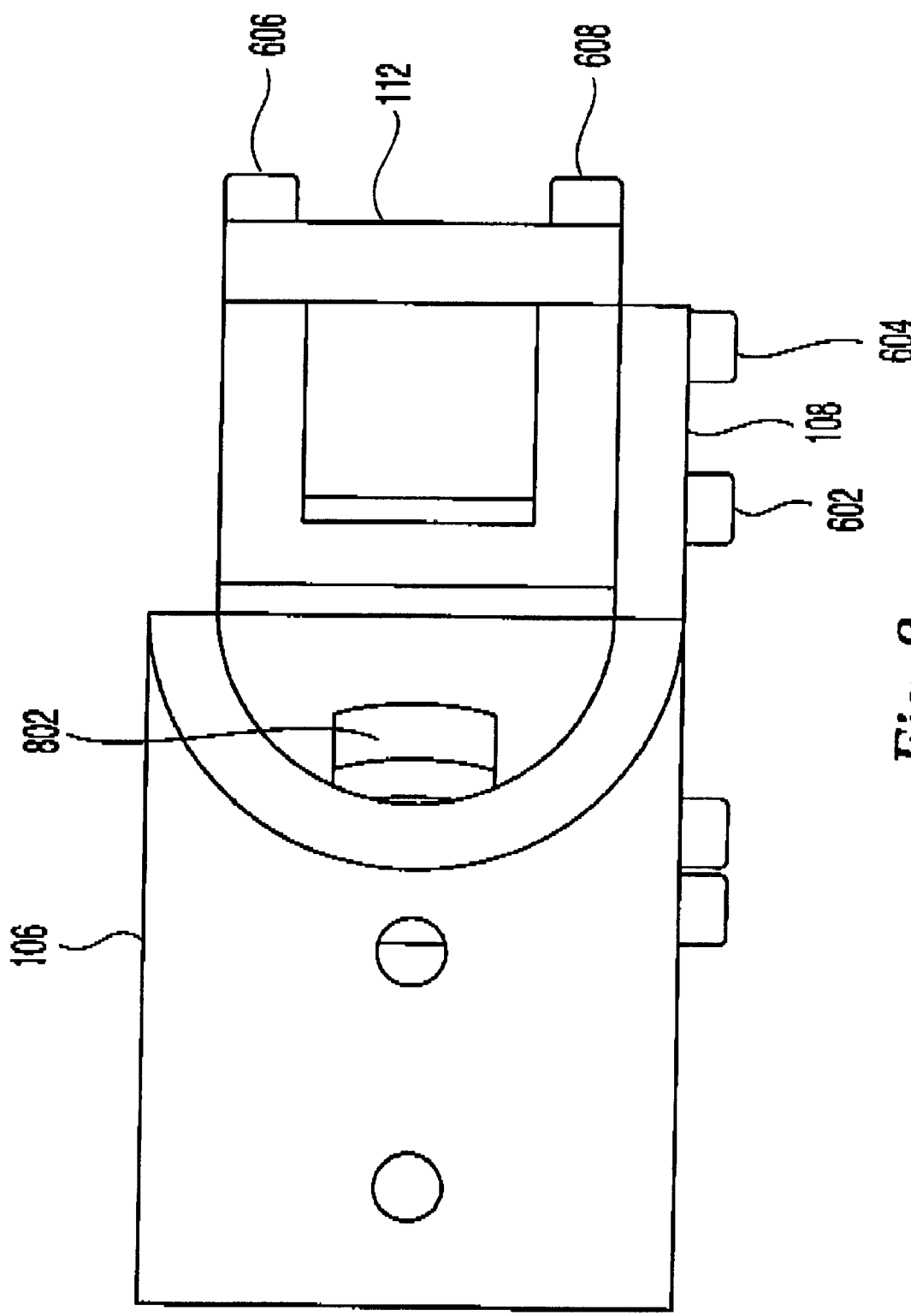
FIG. 8 illustrates a partial top view of an exemplary in-situ residual stress measuring device in accordance with an embodiment of the invention.

FIG. 8 illustrates a partial top view of the improved PSSD 100 in accordance with an embodiment of the invention. This view shows an opening 802 where the x-rays from the x-ray tube 104 exits the tube sleeve 106 into the collimator 107. As explained above in FIG. 7, the mechanical means shown in FIG. 8 are optional depending on how the improved PSSD is manufactured.

Figure 9:
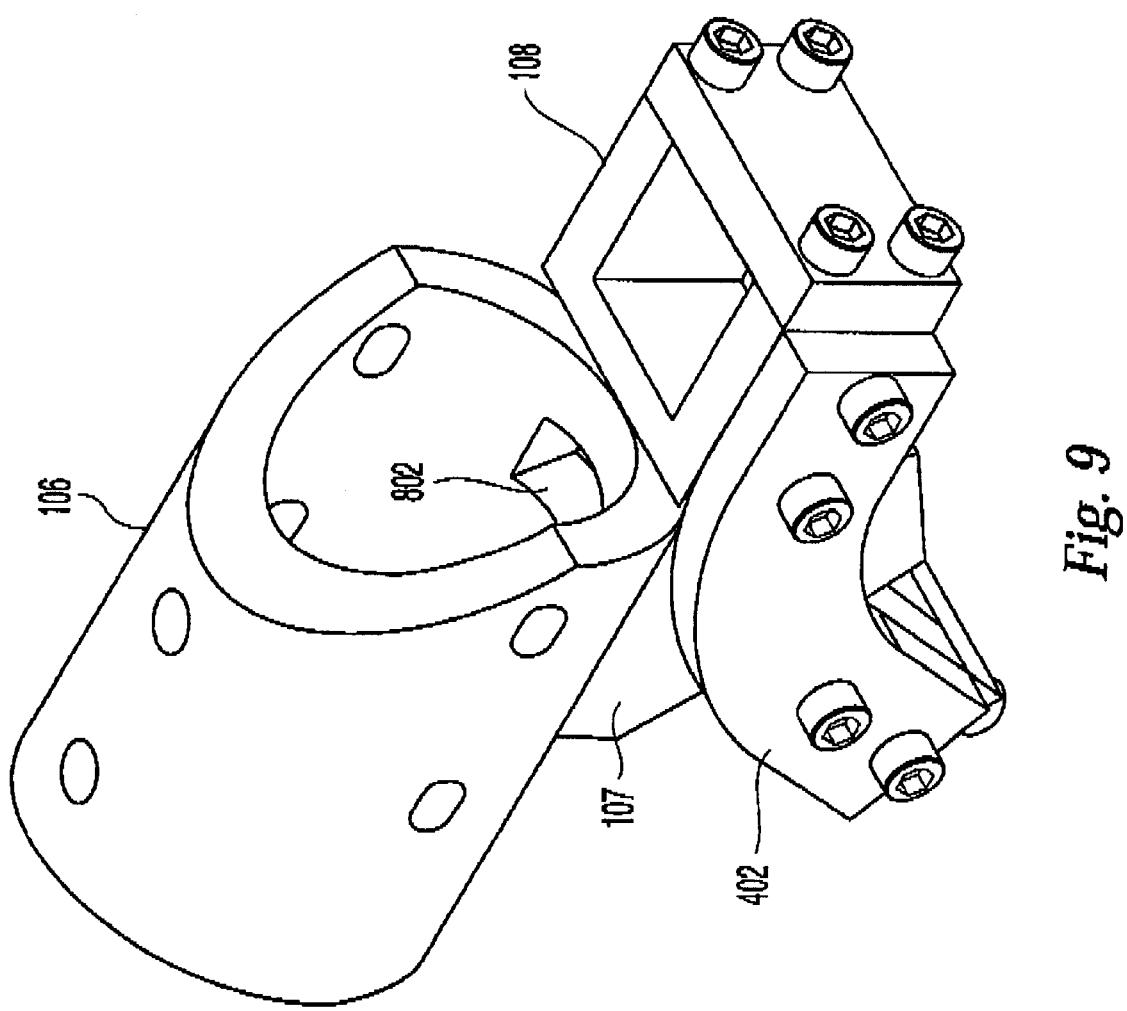
FIG. 9 illustrates a partial left view of an exemplary in-situ residual stress measuring device from the anode side of an x-ray tube in accordance with an embodiment of the invention.

FIG. 9 illustrates a partial left view of the improved PSSD 100 taken from the anode end of the x-ray tube 104 in accordance with an embodiment of the invention. As explained above in FIG. 7, the mechanical means shown in FIG. 9 are optional depending on how the improved PSSD is manufactured.

Figure 10:
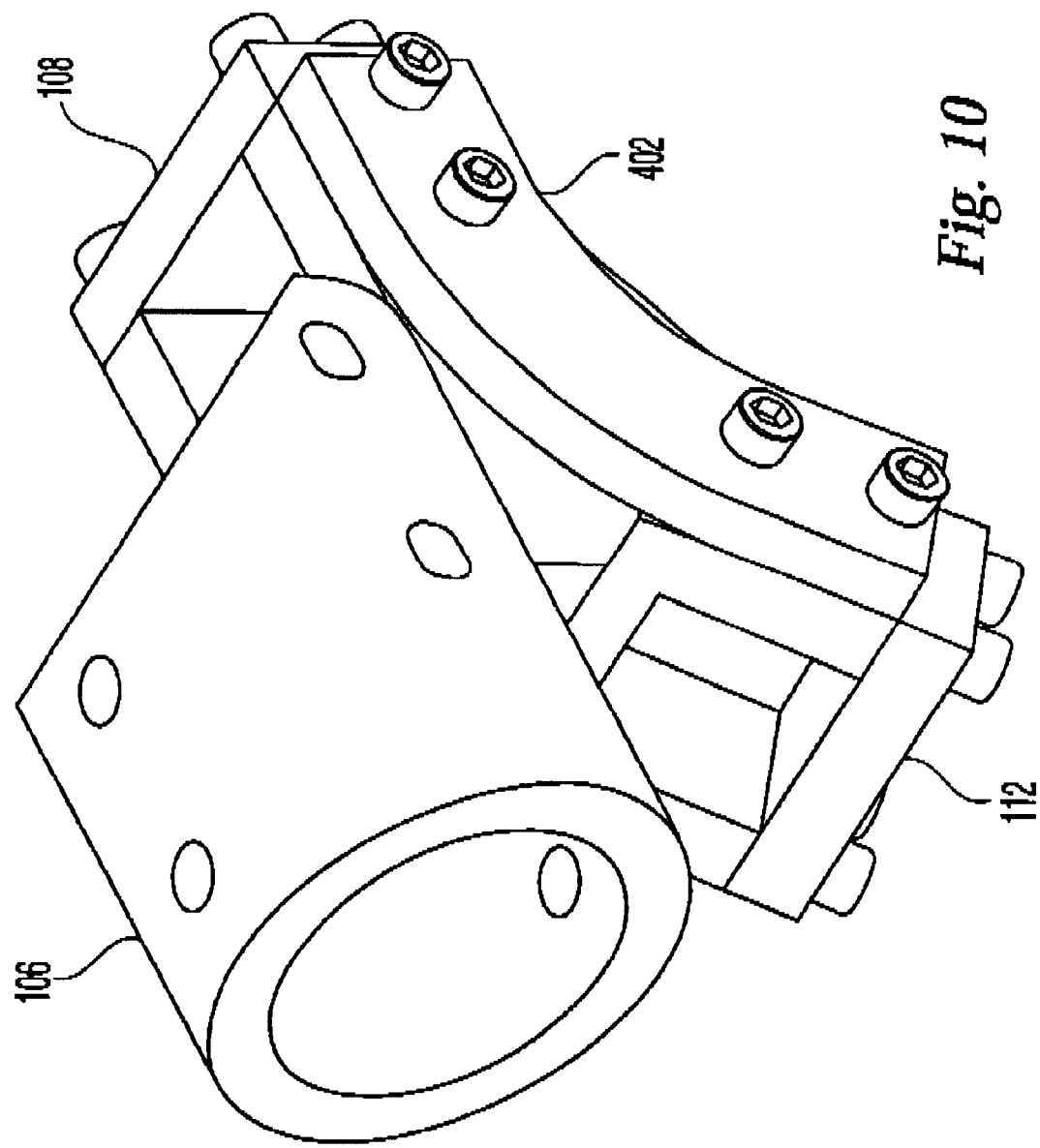
FIG. 10 illustrates another partial left view of an exemplary in-situ residual stress measuring device from the cathode side of an x-ray tube in accordance with an embodiment of the invention.

FIG. 10 illustrates a partial left view of the improved PSSD 100 taken from the cathode end of the x-ray tube 104 in accordance with an embodiment of the invention. This view shows the exemplary support means 402 being used to support both holder A 108 and holder B. As explained above in FIG. 7, the mechanical means shown in FIG. 10 are optional depending on how the improved PSSD is manufactured.

Software for Performing the Stress Analysis

Figure 11:
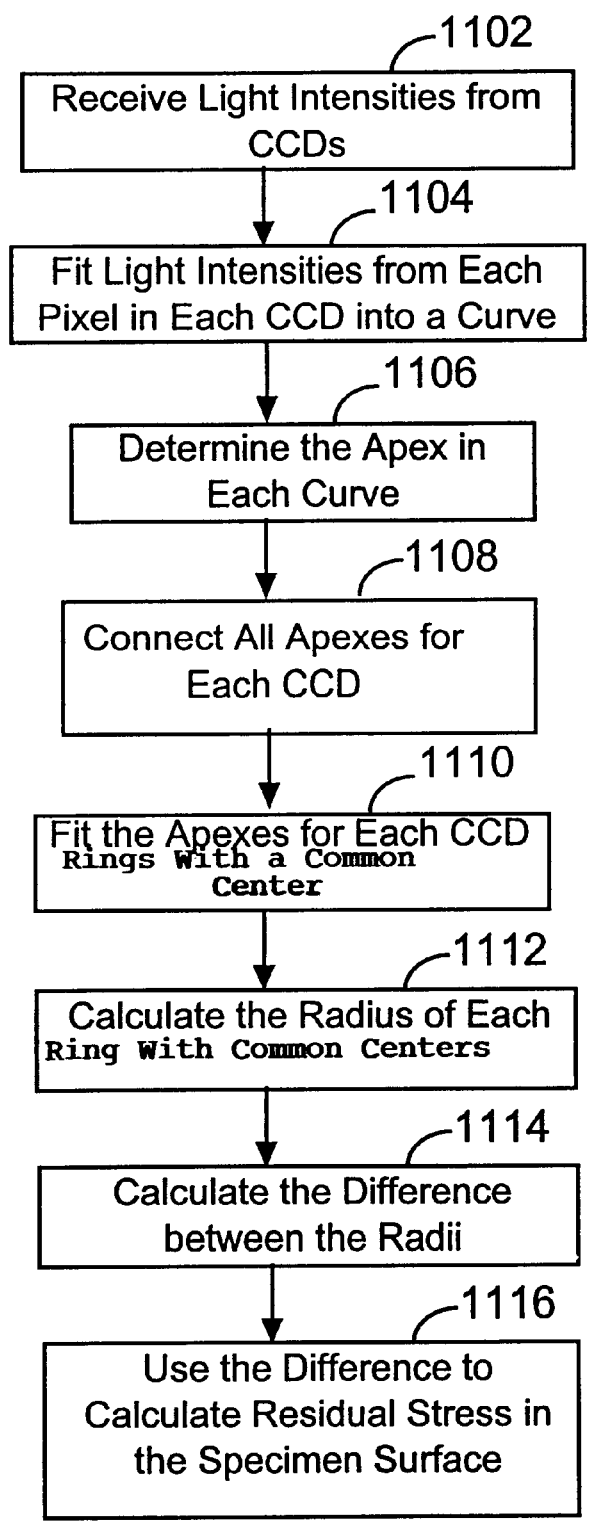
FIG. 11 is a flow chart illustrating an exemplary process to perform stress analysis in accordance with an embodiment of the invention.

In an exemplary embodiment, software installed in the memory portion of the computer 124 is executed to calculate stress based on data from the charged coupled devices 122. The simplified algorithm of the software is illustrated in FIG. 11 in accordance with an embodiment of the invention. At step 1102, light intensities detected by each pixel in the charged coupled devices 122 are digitized and received by the computer 124. Next, digitized light intensities in each pixel is fitted to a curve (step 1104). An apex in each curve is determined (step 1106). For each charged coupled device 122, all determined apexes are connected (step 1108). In an exemplary embodiment, the connected apexes is a close proximate of the ring segments diffracted off of the specimen surface and intercepted by the fiber optic bundles 110, 114, respectively. Next, for each segment, the connected apexes are fitted to define a ring (step 1110). In an exemplary embodiment, geometric equations well known in the art are used to define the ring. The radius of each ring defined in step 1110 is calculated (step 1112). The difference between the radii of both rings is calculated (step 1114). The difference between the radii is used to calculate stress in the specimen surface by solving the series of equations as described in the Stress Analysis section above (step 1116).

The foregoing examples illustrate certain exemplary embodiments of the invention from which other embodiments, variations, and modifications will be apparent to those skilled in the art. The invention should therefore not be limited to the particular embodiments discussed above, but rather is defined by the claims.

What is claimed is:

1. An apparatus for in-situ measurement of residual surface stresses, comprising:
   a compact x-ray tube;
   a tube sleeve coupled to said compact x-ray tube;
   a first fiber optic bundle coupled to said tube sleeve;
   a second fiber optic bundle coupled to said tube sleeve;
   a charged coupled device coupled to said first fiber optic bundle; and
   second fiber optic bundle;
   wherein x-rays emitted by said x-ray tube are diffracted from a specimen surface and intercepted by said first fiber optic bundle and said second fiber optic bundle;
   wherein said intercepted x-rays are converted into light and transferred by said first fiber optic bundle and second fiber optic bundle to said charged coupled device;
   wherein intensities of said received light are detected and digitized to generate a first ring and a second ring; and
   wherein the residual stress in said specimen surface is calculated based on a difference between the radii of said first ring and said second ring.

2. The apparatus of claim 1, wherein said compact x-ray tube is less than 1 inch in diameter.

3. The apparatus of claim 1, wherein said compact x-ray tube generates at least 20 kilovolt x-rays.

4. The apparatus of claim 1, wherein said compact x-ray tube requires less than 100 watts.

5. The apparatus of claim 1, wherein said tube sleeve is coupled to an anode side of said compact x-ray tube.

6. The apparatus of claim 1, further comprising scintillators attached to the front of said first fiber optic bundle and said second fiber optic bundle for converting said x-rays into light.

7. The apparatus of claim 6, wherein said scintillators are rare earth scintillators.

8. The apparatus of claim 6, wherein said scintillators are cadium zinc scintillators.

9. The apparatus of claim 1, wherein said first fiber optic bundle and said second fiber optic bundle comprise fibers each of approximately 10 microns or less in size.

10. The apparatus of claim 1, wherein a cross section of said first fiber optic bundle and said second fiber optic bundle is square.

11. The apparatus of claim 1, wherein said first fiber optic bundle is split into two bundles to travel along said compact x-ray tube and is rejoined before being coupled with the charged couple device.

12. The apparatus of claim 1, wherein said first fiber optic bundle is contoured to fit closely near said compact x-ray tube.

13. The apparatus of claim 1, further comprising an image intensifier positioned between said first fiber optic bundle and said first charged coupled device.

14. The apparatus of claim 13, wherein said image intensifier amplifies light received from said first fiber optic bundle.

15. The apparatus of claim 1, further comprising an image intensifier positioned between said second fiber optic bundle and said charged coupled device.

16. The apparatus of claim 15, wherein said image intensifier amplifies light received from said second fiber optic bundle.

17. The apparatus of claim 1, wherein each of said charged coupled device said second charged coupled device comprises a plurality of pixels and each said pixels detects photons striking the surface of the pixel.

18. The apparatus of claim 1, wherein said residual stress is calculated by a computer attached to receive digitized data from said first and said charged coupled device.

19. The apparatus of claim 1, further comprising a collimator attached to said tube sleeve for collimating x-rays from said x-ray tube onto said specimen surface.

20. The apparatus of claim 1, wherein said first fiber optic bundle and said second fiber optic bundle are coupled to said tube sleeve via mechanical means.

21. The apparatus of claim 1, wherein said first fiber optic bundle and said second fiber optic bundle are coupled to said tube sleeve via adhesive means.

22. A method for in-situ measurement of residual surface stresses, comprising the steps of:
   intercepting a first segment of x-rays diffracted off of a specimen surface;
   intercepting a second segment of said x-rays diffracted off of said specimen surface;
   converting said segments into light;
   detecting intensities in said light from said first segment via a charged coupled device;
   detecting intensities in said light from said second segment via a charged coupled device;
   defining a first ring based on intensities detected by said charged coupled device;
   defining a second ring based on intensities detected by said charged coupled device;
   calculating a first and second radius of said rings with a common center;
   calculating a difference between said first radius and said second radius; and
   calculating residual stress of said specimen surface based on said difference.

23. The method of claim 22, wherein said step of converting said segments into light includes the steps of:

converting said first segment into light via a first scintillation coating; and converting said second segment into light via a second scintillation coating.

24. The method of claim 23, further comprising the steps of:

amplifying said light converted by said first scintillation coating via an image intensifier; and amplifying said light converted by said second scintillation coating via an image intensifier.

25. The method of claim 22, wherein said step of defining a first ring includes the steps of:

fitting said intensities detected by said first charged coupled device into a set of curves;

determining apexes in said set of curves; and connecting said apexes to define said first ring.

26. The method of claim 22, wherein said step of defining a second ring includes the steps of:

fitting said intensities detected by said second charged coupled device into a set of curves;

determining apexes in said set of curves; and connecting said apexes to define said second ring.

* * * * *